United States Patent
Weiss et al.

(10) Patent No.: US 9,295,419 B2
(45) Date of Patent: Mar. 29, 2016

(54) METHOD AND SYSTEM FOR A NON-INVASIVE MEASUREMENT OF OPTICALLY ACTIVE COMPONENT CONCENTRATION

(71) Applicant: T.G.M. Technologies LTD., Kiryat Bialik (IL)

(72) Inventors: Aryeh Uri Weiss, Kiryat Yam (IL); Nataly Oren, Kiryat Bialik (IL); Eitan Koren, Natzeret Illit (IL)

(73) Assignee: T.G.M. TECHNOLOGIES LTD, Kiryat Bialik (IL)

( * ) Notice: Subject to any disclaimer, the term of this patent is extended or adjusted under 35 U.S.C. 154(b) by 265 days.

(21) Appl. No.: 13/887,417

(22) Filed: May 6, 2013

(65) Prior Publication Data

US 2014/0330097 A1    Nov. 6, 2014

(51) Int. Cl.
*A61B 5/1455* (2006.01)
*A61B 5/145* (2006.01)
*A61B 5/00* (2006.01)

(52) U.S. Cl.
CPC ............ *A61B 5/1455* (2013.01); *A61B 5/14532* (2013.01); *A61B 5/14558* (2013.01); *A61B 5/72* (2013.01); *A61B 5/682* (2013.01); *A61B 5/6816* (2013.01); *A61B 5/6819* (2013.01); *A61B 5/6825* (2013.01)

(58) Field of Classification Search
CPC ............. A61B 5/1455; A61B 5/14532; A61B 5/6816; A61B 5/6819; A61B 5/682; A61B 5/0004; A61B 5/72
See application file for complete search history.

(56) References Cited

U.S. PATENT DOCUMENTS

| | | | |
|---|---|---|---|
| 4,467,204 A | 8/1984 | Kysilka et al. | |
| 4,589,776 A | 5/1986 | Carver et al. | |
| 5,168,326 A | 12/1992 | Tokieda et al. | |
| 5,383,452 A | 1/1995 | Buchert | |
| 5,687,721 A | 11/1997 | Kuhls | |
| 5,920,393 A * | 7/1999 | Kaplan | 600/316 |
| 6,775,564 B1 | 8/2004 | Peters et al. | |
| 2013/0033707 A1 | 2/2013 | Yamada et al. | |

FOREIGN PATENT DOCUMENTS

| | | |
|---|---|---|
| WO | 9930132 | 6/1999 |
| WO | 0184121 | 11/2001 |

* cited by examiner

*Primary Examiner* — Eric Winakur
(74) *Attorney, Agent, or Firm* — Mark M. Friedman

(57) ABSTRACT

It is disclosed a device for measuring a concentration of glucose, for example, in a translucent piece of a body, like an earlobe, a tissue connecting two fingers, a nasal ala, or a cheek. The piece is illuminated by a linearly polarized laser beam at a certain polarization direction. Consequently, a diffused radiated light is emitted from the piece, including a directed beam. The device includes a polarizing beam splitter which receives the directed beam, a lens, a sensor array, and means for connecting to a processor. The splitter splits components of the directed beam at two mutually orthogonal linear polarization directions into two polarized beams propagating at two respective different directions. The lens images the distribution of the directed beam on the translucent piece on two spatially separated groups within the sensor arrays. The processor defines pixel pairs from a first and second images which correspond to a same point on the second surface of the translucent piece, and subtracts the first pixels from the respective second pixels to get a difference image. In addition, the processor calculates the variance of the difference image, and calculates the desired concentration accordingly.

20 Claims, 4 Drawing Sheets

METHOD AND SYSTEM FOR A NON-INVASIVE MEASUREMENT OF OPTICALLY ACTIVE COMPONENT CONCENTRATION

BACKGROUND OF THE INVENTION

1. Field of the Invention

The invention is in the field of measurement of component concentration within a tissue. More particularly, the invention relates to a method and system for non-invasive measurement of the concentration of optically active components, such as glucose, in a body tissue.

2. Description of Related Art

Millions of people worldwide suffer from diseases, such as diabetes, that require them to frequently monitor their blood/urine components, such as blood glucose levels. Nowadays, diabetic patients measure their blood glucose levels by using a variety of invasive portable devices. Since the patients need to perform such measurements several times a day, the invasive blood measurements become a burden. In addition, the measurements are often expensive due to disposable tools, such as needles and prickles. As a result, various non-invasive devices have been developed. When used at home, the non-invasive measurement devices enable patients who suffer from diabetes to monitor and respond accordingly to fluctuations in blood glucose levels on a daily basis.

As an example, U.S. Pat. No. 5,687,721 to Kuhls discloses a device and method for non-invasively measuring the concentration of sugar in the blood of a human subject. The method includes generating a beam of monochromatic light, confining the light beam to a predetermined optical path to impinge on a preselected portion of the body of the subject, polarizing the light beam, and performing both a static extinction measurement using the monochromatic light and a dynamic polarization measurement using the polarized light to obtain a measurement of the concentration of sugar in the blood in the preselected body portion. However, according to U.S. Pat. No. 5,687,721 the determination of the concentration of glucose in the blood depends on an absorption coefficient of a test specimen, which in turn leads to significantly inaccurate results, due to an inability to precisely determine such absorption coefficient.

As another example, U.S. Pat. No. 6,775,564 to Peters etal presents a glucose measuring device for determining the concentration of glucose in intravascular blood within a body part of a subject. The device includes a light source having a wavelength of 650, 880, 940 or 1300 nm to illuminate the fluid. A receptor associated with the light source for receiving light and generating a transmission signal representing the light transmitted is also provided. A support piece is included for supporting the light source associated with the respective receptor. The support piece is adapted to engage a body part of a subject. Finally, a signal analyzer determines the glucose concentration in the blood of the subject. However, U.S. Pat. No. 6,775,564 presents a spectro-photometric analysis that relies on the principle that every compound has a unique "pattern" determined by the amount of light absorbed, transmitted, or reflected by the compound at various wavelengths. Unfortunately, the spectro-photometric analysis is only of limited usefulness when the density of the specimen is unknown. These limitations are present because the absorption of light (or the intensity of transmitted light) may be directly affected by these variable factors. Thus, relying solely on the absorption of light at various wavelengths does not yield a sufficiently accurate non-invasive method for analysis of bodily fluids.

U.S. Pat. No. 5,920,393 to Kaplan discloses methods and devices for determining the identity and concentration of constituent compounds within a test specimen. The methods are based on the principle that a specific compound in a specific concentration modifies a pattern of the incident polychromatic light in a manner that is recognizable. The device includes a polychromatic light source directed first through an incident light pattern generator and then through the test specimen. Reflected and transmitted light components then pass through a pattern recognition gating device that selects portions of the light for analysis by an array of detectors. However, in similarity to U.S. Pat. No. 5,687,721, the determination of the concentration of glucose in the blood depends on an absorption coefficient of a test specimen, which in turn leads to significantly inaccurate results due to an inability to precisely determine such absorption coefficient. According to U.S. Pat. No. 5,920,393, when the concentration of optically active component within a test specimen is increased, then the angular distribution of the light beam is changed. However, such change in the angular distribution can be caused because of a change in the absorption coefficient, and not just when said concentration is increased. As a result, using the method of U.S. Pat. No. 5,920,393 for determining the identity and concentration of constituent compounds within a test specimen is relatively inaccurate.

The given method and the system featured in the current invention assumes a possibility of making of an miniature device to be coupled to a body of a person for the continuous monitoring of glucose level in blood. The device serves with an insulin pump a system supporting appropriate glucose level.

Therefore, there is a continuous need to provide a method and system for accurately determining the concentration of an optically active component within a test specimen like a body tissue. Other objects and advantages of the invention will become apparent as the description proceeds.

BRIEF SUMMARY OF THE INVENTION

It is disclosed, according to some preferred embodiments of the current invention, a system for measuring a concentration of an optically active component in a translucent piece of material. The translucent piece has a first and a second opposing surfaces. The system includes a polarizing beam splitter, arrays of light sensors and a processor connected to the arrays of light sensors. The polarizing beam splitter is disposed between the second surface of the translucent piece and the arrays of light sensors.

In operation, the first surface of the translucent piece is illuminated by a monochromatic light beam linearly polarized at a certain polarization direction. A diffused radiated light is emitted from the second surface into a large solid angle, whereas the diffused radiated light includes a directed beam, occupying a relatively small portion of the large solid angle. The splitter receives the directed beam and splits its components at two mutually orthogonal linear polarization directions into two polarized beams propagating at different directions. The arrays of light sensors receive the two polarized beams, respectively, by two spatially separated groups of light sensors. The processor processes the sensed light at the two groups using certain mapping of light sensors in one of the two spatially separated groups to the light sensors in the second group. Finally, the processor calculates the concentration of the optically active material using the sensed light.

In some embodiments, the mapping is made in accordance with a calculation of weighted centers of the two polarized beams. Alternatively, two sensor arrays which detect the two polarized beams have identical sensor layout used for the mapping.

It is disclosed, according to some preferred embodiments of the current invention, a device for measuring a concentration of an optically active component in a translucent piece of material having a first and a second opposing surfaces. The first surface is illuminated by a linearly polarized monochromatic light beam at a certain polarization direction. Consequently, a diffused radiated light is emitted from the second surface, whereas the diffused radiated light includes a relatively directed beam used by the device for measuring the concentration of the optically active component.

The device includes a polarizing beam splitter disposed between the second surface of the translucent piece and arrays of light sensors, a lens disposed between the polarizing splitter and the arrays of light sensors, and means for connecting the arrays of light sensors to a processor.

In operation, the polarizing beam splitter receives the directed beam, and splits its components at two mutually orthogonal linear polarization directions into two polarized beams propagating at two respective different directions. The lens projects the image of the distribution of the directed beam on the second surface of the translucent piece on two spatially separated groups within the arrays of light sensors. Finally, the processor uses the light sensed by the two spatially separated groups for determining the concentration of the optically active component in the translucent piece of material.

In some embodiments, the system includes a diode laser and a linear polarizer disposed between the diode laser and the first surface of the translucent piece of material.

The arrays of light sensors may be the sensors of a charge coupled device (CCD), or the sensors of a complementary metal oxide semiconductor device (CMOS).

In some embodiments, the processor defines pixel pairs whereas in each pair a first pixel is taken from a first image of the distribution of the directed beam on the second surface of the translucent piece, and a second pixel is taken from a second image thereof, such that the first pixel and the second pixel correspond substantially to a same point on the second surface of the translucent piece. Consequently, based on the defined pixel pairs, the processor determines the concentration of the optically active component within the translucent piece. Preferably, the calculation includes a step of subtracting the first pixels from the respective second pixels to get a difference image, a step of adding the first pixels to the respective second pixels to get a sum image, and for non-zero sum image pixels a step of calculating pixel contrast values each equaling a ratio of a difference image pixel and a sum image pixel. Finally, the calculation includes a step of computing a statistical parameter characterizing the variance of the light sensed by the sensor arrays.

In some embodiments, the polarizing splitter is a Wollaston prism.

In some embodiments, the device measures glucose concentration in an earlobe, a tissue connecting two fingers, a nasal ala, or a cheek.

In some embodiments, each of the two mutually orthogonal linear polarization directions has an angle between 40° and 50° relative to the certain polarization direction.

In some embodiments, the system further includes means for coupling the polarizing splitter to the translucent piece.

In some embodiments, the arrays of light sensors are wirelessly connected to the processor.

It is disclosed, according to some preferred embodiments of the present invention, a method for measuring a concentration of an optically active component in a translucent piece of material having a first and a second opposing surfaces. The method includes a first step of illuminating the first surface by a linearly polarized monochromatic light beam at a certain polarization direction such that a diffused radiated light is emitted from the second surface, and the diffused radiated light including a relatively directed beam. The method also includes a step of disposing a polarizing beam splitter between the second surface of the translucent piece and arrays of light sensors, a step of disposing a lens between the polarizing splitter and the arrays of light sensors, such as to image the distribution of the directed beam on the second surface of the translucent piece on two spatially separated groups within the arrays of light sensors, and a step of connecting the arrays of light sensors to a processor. The polarizing beam splitter receives the directed beam and splits its components at two mutually orthogonal linear polarization directions into two polarized beams propagating at two respective different directions. The processor uses the light sensed by the two spatially separated groups for determining the concentration of the optically active component in the translucent piece of material.

BRIEF DESCRIPTION OF THE DRAWINGS

The subject matter regarded as the invention is particularly pointed out and distinctly claimed in the concluding portion of the specification. The invention, however, both as to system organization and method of operation, together with features and advantages thereof, may best be understood by reference to the following detailed description when read with the accompanied drawings in which:

DETAILED DESCRIPTION OF THE INVENTION

Figure 1:
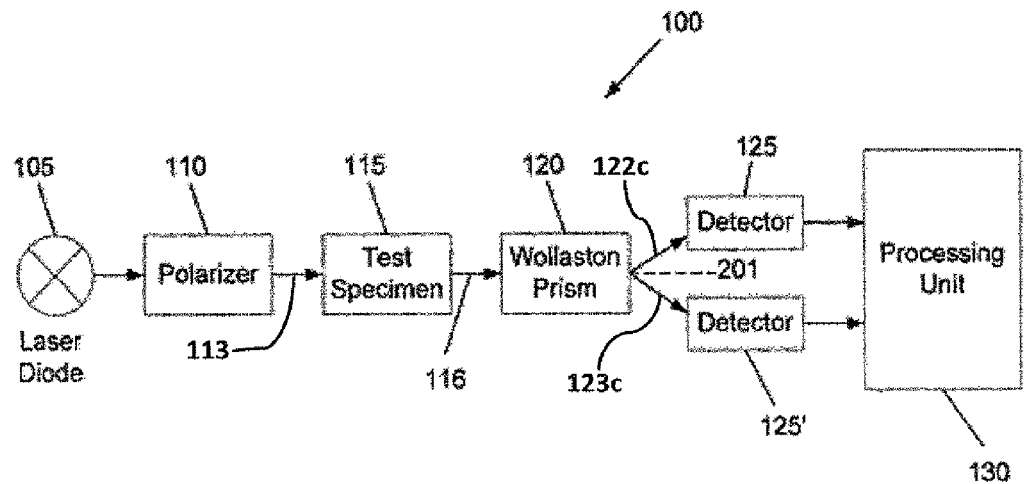
FIG. 1 (PRIOR ART) is a schematic diagram of a set-up for measuring the concentration of an optically active material in a test specimen using a Wollaston prism and two light detectors.

The present invention will now be described in terms of specific example embodiments. It is to be understood that the invention is not limited to the example embodiments disclosed. It should also be understood that not every feature of the methods and systems handling the described device is necessary to implement the invention as claimed in any particular one of the appended claims. Various elements and features of devices are described to fully enable the invention. It should also be understood that throughout this disclosure, where a method is shown or described, the steps of the method may be performed in any order or simultaneously, unless it is clear from the context that one step depends on another being performed first.

Before explaining several embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which this invention belongs. The systems, methods, and examples provided herein are illustrative only and not intended to be limiting.

In the description and claims of the present application, each of the verbs "comprise", "include" and "have", and conjugates thereof, are used to indicate that the object or objects of the verb are not necessarily a complete listing of members, components, elements or parts of the subject or subjects of the verb.

Definitions

Translucent—a semitransparent material which receives a light beam in a first side and emits a diffused light from a second side.

Wollaston prism—an optical device that manipulates polarized light. It separates polarized or non-polarized light into two orthogonal, linearly polarized outgoing beams. The Wollaston prism consists of two orthogonal calcite prisms, cemented together on their base to form two right triangle prisms with perpendicular optical axes. Outgoing light beams diverge from the prism, giving two polarized rays, with the angle of divergence determined by the prisms' wedge angle and the wavelength of the light.

Figure 2A:
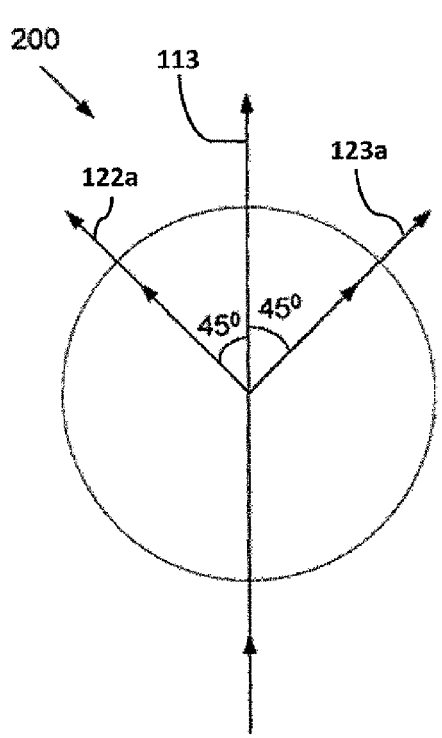
FIG. 2a (PRIOR ART) illustrates beam polarization before entering the Wollaston prism.
Figure 2B:
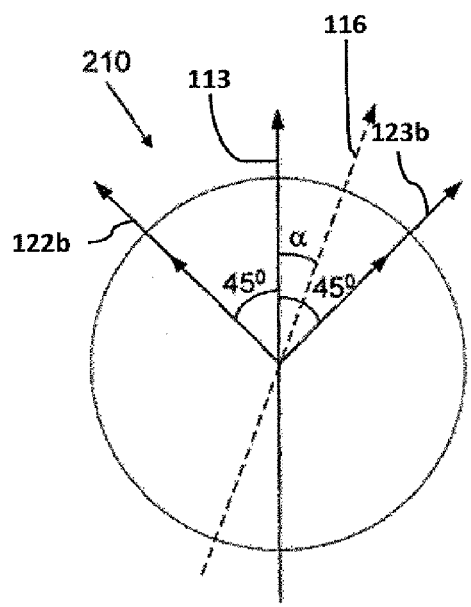
FIG. 2b (PRIOR ART) illustrates beam polarization in the presence of an optically active material in the test specimen.

Prior Art (FIGS. 1,2a and 2b)

Before describing the current invention, FIGS. 1, 2a, and 2b illustrate measurement of optically active concentration in a transparent specimen, as is well known in the prior art. FIG. 1 is a schematic diagram illustration of a system 100, in which a laser diode 105 emits a laser light beam having a predefined wave length (in the range 680-700 nm for example), followed by a linear polarizer 110 such that a linearly polarized beam 113 is obtained. Referring now to the polarization diagram of FIG. 2a, it is assumed that the plane of the layout of FIG. 1 is horizontal, and beam 113 is vertically polarized. Beam 113 is a vectorial sum of a beam 122a polarized at 45° counterclockwise to the vertical direction, and a beam 123b polarized at 45° clockwise to the vertical direction. Regarding beam power, each of beams 122a and 123a has an amplitude $A \cdot \cos(45°)$ where A is the amplitude of beam 113, and thus its beam power is half the beam power of beam 113.

Beam 113 enters test specimen 115 which contains, for instance, a non-scattering solution having certain concentration of an optically active component. The emitted laser beam 116 may keep the spatial direction of beam 113, but the optically active component rotates its polarization direction by an angle α fulfilling $$\alpha = \alpha_0 \cdot C \cdot L \quad (1)$$

wherein $\alpha_0$ is a coefficient of angular rotation of the optically active component, C is its concentration and L is of the width of test specimen 115. Beam 116 is a vectorial sum of beams 122b and 123b which have the same polarization as beams 122a and 123a, respectively. However, beam power has changed due to beam attenuation and rotation in test specimen 115. Thus, the amplitude of beam 122b is $B \cdot \cos(45° + \alpha)$ while the amplitude of beam 123b is $B \cdot \cos(45° - \alpha)$, where B is the amplitude of beam 116. Note that for the case of no rotation α=0 and the amplitude of beam 122b equals the amplitude of beam 123b. But for small α, 20° for example, the amplitude of beam 122b is larger than the amplitude of beam 123b. The size of α may be calculated by measuring the power of beams 122b and 123b, and dividing them respectively to get a ratio R, wherein $$R = \cos^2(45° + \alpha)/\cos^2(45° - \alpha) \quad (2)$$

and α may be calculated without any data on $B^2$. Thus, it is desired to split beam 116 to beams 122b and 123b.

For that sake, beam 116 enters a Wollaston prism 120, which is disposed such that it splits beam 116 to two polarized beam 122c and 123c, where beam 122c is polarized in the same direction as beams 122a and 122b, and beam 123c is polarized in the direction of 123a and 123b. Regarding beam propagation direction, beam 122c is shifted counterclockwise by 9°, for example, relative to an optical axis 201 of the Wollaston prism 120, and light beam 123c is shifted clockwise by 11°, for example, relative to optical axis 201. Since beams 122c and 123c are directionally separated, they hit two separate detectors 125 and 125', which measure their beam powers. The measured beam power of beams 122c and 123c is delivered to processing unit 130, which divides the powers to get rid of beam power, and obtain angle α by solving equation (2), thus providing the proportional concentration of the optically active material.

Alternatively, one may calculate the contrast N of the beam power, namely the difference between the two beam powers divided by their sum, which fulfils $$N = [\cos^2(45° - \alpha) - \cos^2(45° + \alpha)]/[\cos^2(45° - \alpha) + \cos^2(45° + \alpha)] \quad (3)$$

or $$N = 2 \sin \alpha \cos \alpha / [\cos^2(45° - \alpha) + \cos^2(45° + \alpha)] \quad (4)$$

The contrast N is free from the dependence on the beam power and its size increases with angle α. Solving equation (4) to get α may be more accurate comparing to the use of the ratio of beam powers, especially for small values of angle α.

Note that laser diode 105 may be coupled to a lens (not shown) such as to shape the beam as desired. In a preferred embodiment, the lens is located such that the beam has waist at a place like the entrance to the polarizer, the center of the test specimen, etc.

Figure 3A:
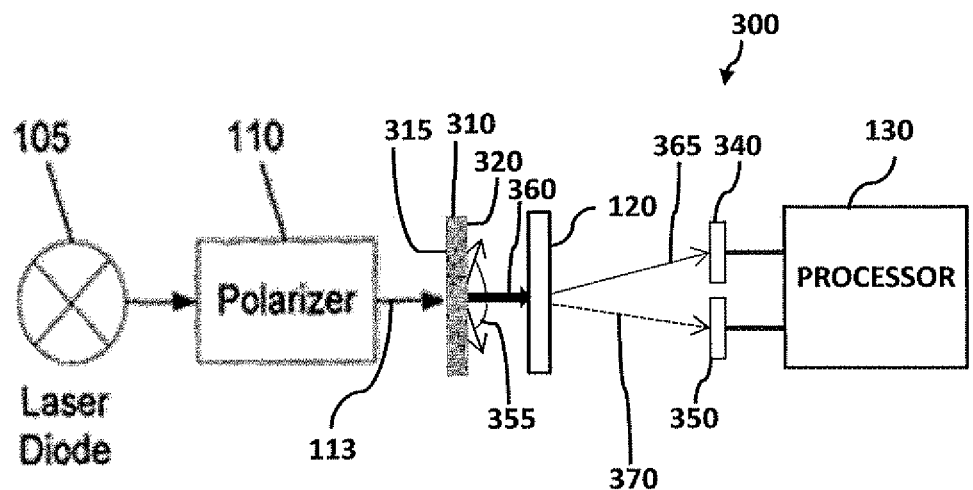
FIG. 3a is a schematic diagram of a set-up for measuring the concentration of an optically active material in a translucent piece of material, according to a first embodiment of the invention.
Figure 3B:
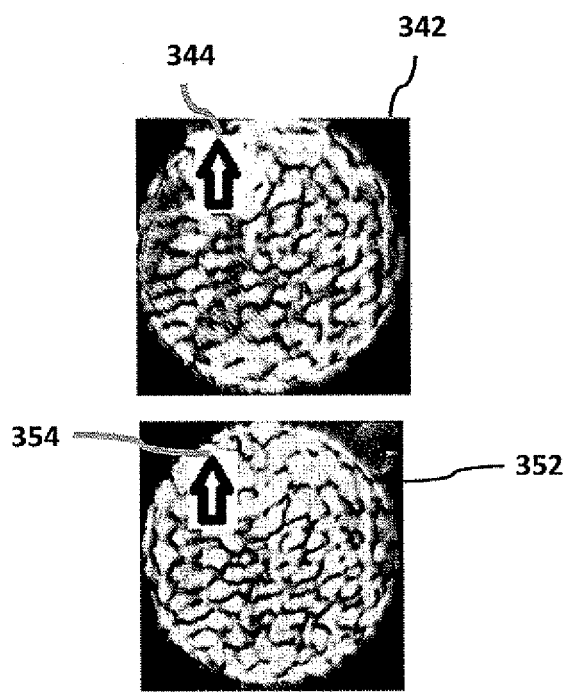
FIG. 3b presents two light distributions sensed in two separated groups of light sensors and mapped to each other.

A System Embodiment with Mapping (FIGS. 3a and 3b)

The present invention is especially aimed at measuring glucose concentration in a human body. For that sake, tissues like an earlobe, a tissue connecting two fingers, a nasal ala, or a cheek may be used. To this aim, the method and system of FIGS. 1,2a and 2b are generalized to a case of a scattering test specimen, whereas the scattering test specimen emits a diffused light beam rather than emitting a well defined beam. Yet, a portion of the diffused beam is directed forward and may be used for the measurement. Innovative computational methods allow accurate determination of the concentration despite the light scattering in the tissue.

A first embodiment is illustrated in FIGS. 3a and 3b, describing a system 300 for measuring a concentration of an optically active component in a translucent piece of material 310. Translucent piece 310 has a first surface 315 and a second opposing surface 320. System 300 includes a polarizing beam splitter 120, and arrays of light sensors 340 and 350 connected to a processor 130. Polarizing beam splitter 120 is disposed between surface 320 of the translucent piece and sensor arrays 340 and 350.

In operation, surface 315 of translucent piece 310 is illuminated by a monochromatic light beam 113 linearly polarized at a certain polarization direction. A diffused radiated light is emitted from the second surface into a large solid angle 355 which may approach $2\pi$ steradians. The diffused radiated light includes a directed beam 360, occupying a relatively small portion of solid angle 355. Splitter 120 receives directed beam 360 and splits its components at two mutually orthogonal linear polarization directions into two polarized beams 365 and 370 propagating at two different directions. Arrays 340 and 350 are located far enough from splitter 120 to receive the two polarized beams by two spatially separated groups of light sensors 342 and 352, respectively, as depicted in FIG. 3b.

Arrays 340 and 350 may be a charge coupled device (CCD), or a complementary metal oxide semiconductor device (CMOS).

For the calculation, sensor group 342 is mapped to sensor group 352. For example, in FIG. 3b a pixel 344 of sensor group 342, indicated by the arrow, is mapped to a pixel 354 of sensor group 352, indicated by a similar arrow. The mapping may be made by a calculation of centers of the two polarized beams, whereas a center is calculated as a pixel power weighted center. Alternatively, two sensor arrays 340 and 350 which detect the two polarized beams may have an identical sensor layout (not shown), 500×600 pixels for example, and pixel (32,49) in array 340 is mapped to pixel (32,49) in array 350, for example.

A variety of parameters associated with angle $\alpha$ and/or concentration of the optically active material may be calculated from the sensed light, including a difference map, an integrated difference map, a contrast map, a standard deviation of the difference map, and a standard deviation of the contrast map. Angle $\alpha$ and/or concentration of the optically active material may be proportional to at least one of the calculated parameters, or may has more complicated dependence on these parameters.

For example, denoting the standard deviation of the entries in the difference map by S, the average value of the entries in the difference map by D and the concentration of the optically active material by C, it is assumed that $$C = a_1 \cdot S \text{ and } a_2 \cdot D \quad (5)$$

wherein the coefficients $a_1$ and $a_2$ may be determined experimentally.

It should be noted that instead of Wollaston prism 120, any prism that separates light into two polarized beams outgoing in different directions may be used.

Figure 4:
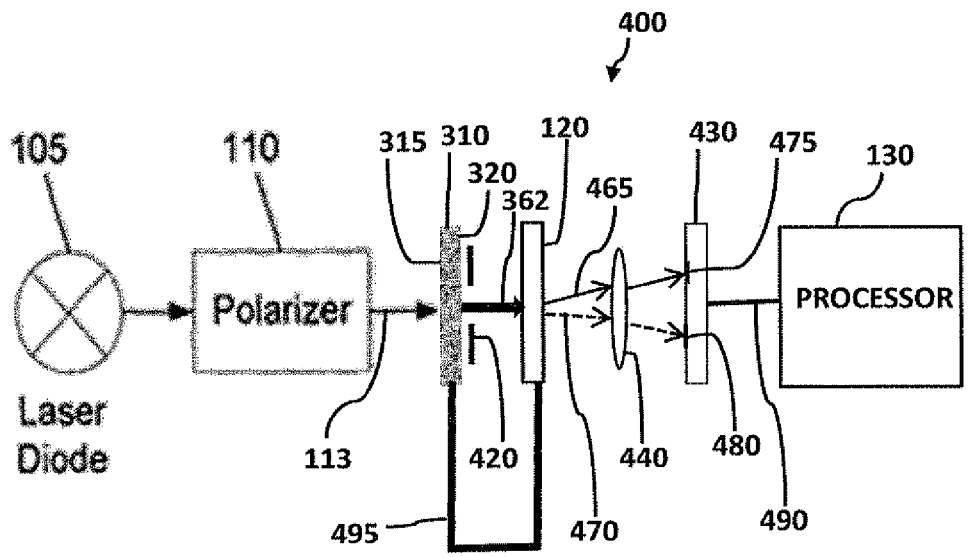
FIG. 4 is a schematic drawing of a set-up for measuring the concentration of an optically active material in a translucent piece of material using image mapping.
Figure 5:
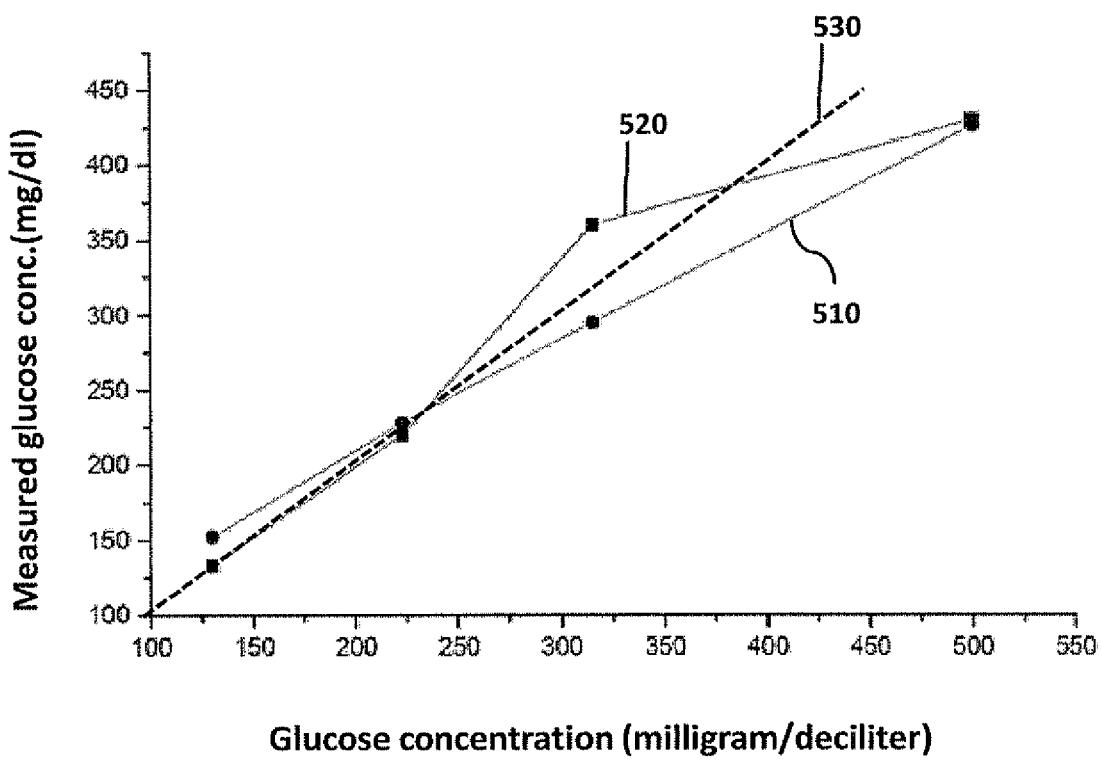
FIG. 5 shows glucose concentration measurements by a commercial glucometer and by the method of the present invention as function of the actual glucose concentration.

A Device Embodiment with Imaging (FIGS. 4,5)

A device 400 for measuring a concentration of an optically active component in a translucent piece of material 310 is presented in the schematic diagram of FIG. 4. Surface 315 is illuminated by a linearly polarized monochromatic light beam 113 at a certain polarization direction. Consequently, a diffused radiated light 355 (FIG. 3a) is emitted from surface 320, whereas diffused radiated light 355 includes a relatively directed beam 362 used by device 400 for measuring the concentration of the optically active component. An iris 420 defines the portion of surface 320 emitting the directed beam, while its angular spread is defined while it propagates along device 400.

A polarizing beam splitter 120, a Wollaston prism for example, is disposed after surface 320 of translucent piece 310, followed by a lens 440, and an array 430 of light sensors. Array 430 is connected to a processor 130 by a channel 490.

A base 495 may mechanically couple splitter 120 to translucent piece 310. For using an earlobe, device 400 may be shaped as an earring which includes a polarized laser 105, a splitter 120, a lens 440 and a sensor array 480, having a wireless connection 490 with a remote processor.

In operation, polarizing beam splitter 120 receives directed beam 362, and splits its components at two mutually orthogonal linear polarization directions into two polarized beams 465 and 470 propagating at two respective different directions. Lens 440 projects the image of the distribution of directed beam 362 on surface 320 on two spatially separated groups 475 and 480 within array 430. The sensed light is transmitted by channel 490 to processor 130, and processor 130 uses the light sensed by the two spatially separated groups for determining the concentration of the optically active component in the translucent piece of material. The concentration determination is based on the image mapping to a same distribution of light on surface 320 of said translucent piece of material.

For the mapping, processor 130 may define pixel pairs whereas in each pair a first pixel is taken from group 475, and a second pixel is taken from group 480, such that the first pixel and the second pixel correspond substantially to a same point on surface 320 of translucent piece 310. Consequently, based on the defined pixel pairs, processor 130 determines the desired concentration by steps like subtracting the first pixels from the respective second pixels to get a difference image, adding the first pixels to the respective second pixels to get a sum image, and for non-zero sum image pixels, calculating pixel contrast values each equaling a ratio of a difference image pixel and a sum image pixel. In addition, the calculation may include computing a statistical parameter characterizing the variance of the light sensed by the sensor arrays, like the standard deviation of the difference map or the contrast map.

Rather than being exactly at 45° relative to the polarization direction of beam 113, each of the two mutually orthogonal linear polarization directions may has an angle between 40° and 50° with the polarization of beam 113. In other words, the angle between the optical axis of polarizer 110 and the optical axis 122a and 122b of Wollaston prism 120 is 45°, or alternatively between 40° and 50°.

FIG. 5 illustrates a typical measurement 510 of the concentration of glucose using the present non-invasive method, in comparison with a measurement 520 done using an invasive stick method. Also shown is a line 530 which represents an ideal measurement which retrieve the glucose concentration accurately.

Figure 6:
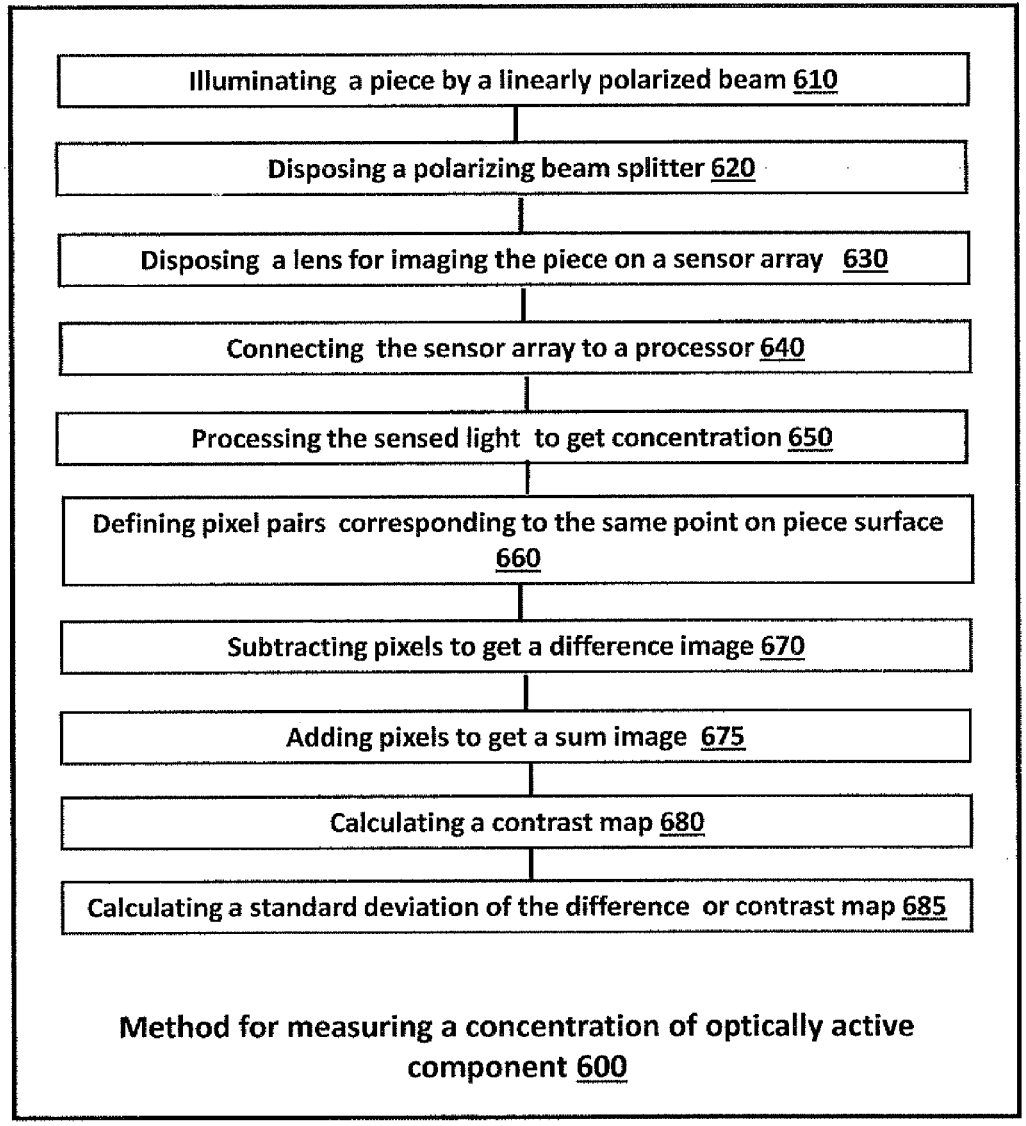
FIG. 6 is a flow chart of a method for measuring the concentration of an optically active material.

A Method Embodiment with Imagine (FIG. 6)

FIG. 6 presents a flow chart of a method 600 for measuring a concentration of an optically active component in a translucent piece 310 of material having a first surface 315 and a second opposing surface 320. Method 600 includes a step 610 of illuminating surface 315 by a linearly polarized monochromatic light beam 113 at a certain polarization direction such that a diffused radiated light 355 is emitted from surface 320, and diffused radiated light 355 includes a relatively directed beam 362. Method 600 also includes a step 620 of disposing a polarizing beam splitter 120 between surface 320 and an array 430 of light sensors, a step 630 of disposing a lens 440 between splitter 120 and sensor array 430, such as to image the distribution of directed beam 362 on surface 320 on two spatially separated groups 475 and 480 within array 430, and a step 640 of connecting array 430 to a processor 130. Polarizing beam splitter 120 receives directed beam 362 and splits its components at two mutually orthogonal linear polarization directions into two polarized beams 465 and 470 propagating at two respective different directions. Method 600 also includes a step 650 of processing the sensed light by the two spatially separated groups 475 and 480 for determining the concentration of the optically active component in translucent piece 310.

For the mapping, method 600 includes a step 660 of defining pixel pairs whereas in each pair a first pixel is taken from group 475, and a second pixel is taken from group 480, such that the first pixel and the second pixel correspond substantially to a same point on surface 320 of translucent piece 310. Based on the defined pixel pairs, method 600 further includes a step 670 of subtracting the first pixels from the respective second pixels to get a difference image, and a step 675 of adding the first pixels to the respective second pixels to get a sum image. For non-zero sum image pixels, method 600 may include a step 680 of calculating pixel contrast values each equaling a ratio of a difference image pixel and a sum image pixel. In addition, method 600 may include a step 680 of computing a standard deviation of the difference map or of the contrast map.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In particular, the present invention is not limited in any way by the examples described.

The invention claimed is:

1. A system for measuring a concentration of an optically active component in a translucent piece of material having a first and a second opposing surfaces, the device comprising:
   (a) a polarizing beam splitter configured to receive a directed beam from the second surface and to split components of the received directed beam at two mutually orthogonal linear polarization directions into a first and a second polarized beams propagating at different directions such that said first polarized beam is directed to a first group of light sensors, and said second polarized beam is directed to a second group of light sensors;
   (b) said first and second group of light sensors are two spatially separated groups of light sensors; and
   (c) a processor connected to said first group of light sensors and said second group of light sensors, said processor configured for processing the sensed light at said two groups using mapping of light sensors in one of said two spatially separated groups to the light sensors in a second group thereof,
   and said processor is configured for calculating the concentration of the optically active material using said mapping result of measured sensed light.

2. The system of claim 1 wherein the system includes a diode laser and a linear polarizer configured to be disposed between said diode laser and the first surface of said translucent piece of material.

3. The system of claim 1 wherein one or more lenses are disposed between the polarizing splitter and said one or more arrays of light sensors said one or more lenses being configured to image the distribution of the directed beam on the translucent piece on two spatially separated groups within the sensor.

4. The system of claim 1 wherein said light sensors are selected from the group of sensors consisting of:
   (A) charge coupled device sensors; and
   (B) complementary metal oxide semiconductor sensors.

5. The system of claim 1 wherein the system includes a Wollaston prism for polarized splitting.

6. The system of claim 1 wherein the system is configured to measure glucose concentration by light illumination of a tissue selected from a group of tissues consisting of an earlobe, a tissue connecting two fingers, a nasal ala, and a cheek.

7. The system of claim 1 wherein each of said two mutually orthogonal linear polarization directions has an angle between 40° and 50° relative to said certain polarization direction.

8. The system of claim 1 wherein the system further includes means for coupling the polarizing splitter to said translucent piece.

9. The system of claim 1 wherein said sensors are wirelessly connected to said processor.

10. The system of claim 1 wherein said mapping is made in accordance with a calculation of weighted centers of the two polarized beams.

11. The system of claim 1 wherein two sensor arrays detecting said two polarized beams have identical sensor layout used for said mapping.

12. A device for measuring a concentration of an optically active component in a translucent piece of material having a first and a second opposing surfaces, the first surface being illuminated by a linearly polarized monochromatic light beam at a certain polarization direction, a diffused radiated light being emitted from the second surface, the diffused radiated light including a relatively directed beam used by the device for measuring the concentration of the optically active component, the device comprising:
   (a) a polarizing beam splitter configured to receive the directed beam from the second surface and to split components of the received beam at two mutually orthogonal linear polarization directions into first and a second polarized beams propagating at two respective different directions such that said first polarized beam is directed to a first group of light sensors, and said second polarized beam is directed to a second group of light sensors;
   (b) one or more lenses disposed between the polarizing splitter and said light sensors, such as to image the distribution of said directed beam on the second surface of said translucent piece on two spatially separated groups within said light sensors; and
   (c) a processor configured for using the light sensed by said two spatially separated groups for determining the concentration of the optically active component in said translucent piece of material, based on the image mapping to a same distribution of light on the second surface of said translucent piece of material.

13. The device of claim 12 wherein the processor is adapted for:
   (i) defining pixel pairs having each a first pixel from a first image of the distribution of said directed beam on the second surface of said translucent piece, and a second pixel from a second image thereof, said first pixel and said second pixel corresponding substantially to a same point on the second surface of said translucent piece; and
   (ii) determining the concentration of said optically active component within said translucent piece based on the defined pixel pairs.

14. The device of claim 13 wherein said processor is further adapted for at least one calculating step of a group of calculating steps consisting of:
   (iii) subtracting the first pixels from the respective second pixels to get a difference image;
   (iv) adding the first pixels to the respective second pixels to get a sum image;

(v) for non-zero sum image pixels, calculating pixel contrast values each equaling a ratio of a difference image pixel and a sum image pixel; and (vi) calculating a statistical parameter characterizing the variance of the light sensed by said sensor.

15. The device of claim 12 wherein the polarizing splitter is a Wollaston prism.

16. The device of claim 12 wherein the device measures glucose concentration by light illumination of a tissue selected from a group of tissues consisting of an earlobe, a tissue connecting two fingers, a nasal ala, and a cheek.

17. The device of claim 12 wherein each of said two mutually orthogonal linear polarization directions have an angle between 40° and 50° relative to said certain polarization direction.

18. The device of claim 12 wherein the system further includes means for coupling the polarizing splitter to said translucent piece.

19. The device of claim 12 wherein said light sensors are wirelessly connected to said processor.

20. A method for measuring a concentration of an optically active component in a translucent piece of material having a first and a second opposing surfaces, the method comprising:

(a) illuminating the first surface by a linearly polarized monochromatic light beam at a certain polarization direction such that a diffused radiated light being emitted from the second surface, the diffused radiated light including a relatively directed beam;

(b) disposing a polarizing beam splitter between the second surface of said translucent piece and one or more arrays of light sensors, said polarizing beam splitter being configured to receive the directed beam and to split components of the received beam at two mutually orthogonal linear polarization directions to two polarized beams propagating at two respective different directions;

(c) disposing one or more lenses between the polarizing splitter and said one or more arrays of light sensors, such as to image the distribution of said directed beam on the second surface of said translucent piece on two spatially separated groups within said one or more arrays of light sensors; and (d) determining the concentration of the optically active component in said translucent piece of material by mapping images of the light sensed by said two spatially separated groups to a same distribution of light on the second surface and calculating the concentration using said mapping result.

* * * * *